United States Patent
Kuhn et al.

(10) Patent No.: US 10,823,953 B2
(45) Date of Patent: Nov. 3, 2020

(54) VIDEO ENDOSCOPE

(71) Applicant: Scholly Fiberoptic GmbH, Denzlingen (DE)

(72) Inventors: Matthias Kuhn, Freiburg (DE); Massimo Kubon, Emmendingen (DE); Jochen Dietrich, Elzach (DE); Maximilian Gotz, Freiburg (DE); Johannes Wickersheim, Malterdingen (DE); Patrick Spring, Freiburg (DE); Harald Haigis, Elzach (DE); Mateusz Cichosz, Freiburg i. Br. (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 35 days.

(21) Appl. No.: 16/015,729

(22) Filed: Jun. 22, 2018

(65) Prior Publication Data
US 2019/0056583 A1 Feb. 21, 2019

(30) Foreign Application Priority Data
Aug. 18, 2017 (DE) .................. 10 2017 118 941

(51) Int. Cl.
| | |
|---|---|
| H04N 7/18 | (2006.01) |
| A62B 1/04 | (2006.01) |
| A61B 1/04 | (2006.01) |
| A61B 1/06 | (2006.01) |
| G02B 23/24 | (2006.01) |
| A61B 1/12 | (2006.01) |
| A61B 1/05 | (2006.01) |
| H04N 5/225 | (2006.01) |
| A61B 1/00 | (2006.01) |
| G02B 23/26 | (2006.01) |

(52) U.S. Cl.
CPC ............ *G02B 23/2476* (2013.01); *A61B 1/05* (2013.01); *A61B 1/0676* (2013.01); *A61B 1/128* (2013.01); *G02B 23/2423* (2013.01); *G02B 23/2461* (2013.01); *G02B 23/2484* (2013.01); *H04N 5/2256* (2013.01); *A61B 1/00066* (2013.01); *G02B 23/2469* (2013.01); *G02B 23/26* (2013.01); *H04N 2005/2255* (2013.01)

(58) Field of Classification Search
USPC ......... 348/65, 61, 73, 79; 600/112, 109, 178
See application file for complete search history.

(56) References Cited

U.S. PATENT DOCUMENTS

| | | | |
|---|---|---|---|
| 9,510,744 B2 | 12/2016 | Schrader et al. | |
| 9,757,019 B2 | 9/2017 | Pilz et al. | |
| 2011/0306834 A1* | 12/2011 | Schrader | A61B 1/00066 600/112 |

(Continued)

FOREIGN PATENT DOCUMENTS

| | | |
|---|---|---|
| DE | 102014107205 | 11/2015 |
| DE | 102014209980 | 11/2015 |
| EP | 2394567 | 12/2011 |

*Primary Examiner* — Daquan Zhao
(74) *Attorney, Agent, or Firm* — Volpe Koenig

(57) ABSTRACT

An endoscope (1) with an endoscope shaft (3) in which an illumination device (11) and a rotatably mounted image sensor (12) are arranged in a distal region (8) is provided, and includes a handle (2) in which a rotatably mounted heat sink (16) is arranged, wherein the image sensor (12) is thermally connected to the heat sink (16), for conjoint rotation therewith, via a heat transmission element (15).

19 Claims, 4 Drawing Sheets

(56) References Cited

U.S. PATENT DOCUMENTS

2015/0080649 A1* 3/2015 Ayrenschmalz ..... A61B 1/0016
　　　　　　　　　　　　　　　　　　　　　　600/102
2017/0071462 A1　3/2017 Wieters et al.

* cited by examiner

VIDEO ENDOSCOPE

INCORPORATION BY REFERENCE

The following documents are incorporated herein by reference as if fully set forth: German Patent Application No. 10 2017 118 941.6, filed Aug. 18, 2017.

BACKGROUND

The invention relates to an endoscope with an endoscope shaft which, in a distal region, has an illumination device and an image sensor mounted rotatably with respect to the endoscope shaft, and with a handle or (rotary) wheel which is connected to the proximal end of the endoscope shaft.

Endoscopes of this kind are known and are in particular used when an optics unit formed in the distal region defines a captured viewing range with respect to the longitudinal axis of the endoscope shaft. In this case, the rotatability of the image sensor serves to generate a spatially fixed horizon upon rotation of the viewing range.

In the prior art, the image sensor is often based on a CCD (charge coupled device), as described for example in DE 10 2014 209 980 A1. An image sensor based on a CCD has the advantage that it has only slight heat development. This is particularly important in image sensors that are arranged in the distal region of the endoscope shaft, since here a regulatory standard governs the maximum heat output.

Image sensors based on a CCD, however, have only low light sensitivity and resolution. For this reason, it is desirable to use CMOS-based image sensors, as are now customary in digital cameras and smartphones.

However, these CMOS image sensors have the disadvantage that they have a greater heat output and therefore, in order to meet the regulatory standards, they require better cooling or heat dissipation, which can be achieved only with difficulty within the limited available installation space of the endoscope shaft.

In addition, the use of more powerful light-emitting diodes or laser diodes is also desirable, since these are able to substantially improve the degree of illumination and the contrast. However, these light-emitting diodes also develop a high level of waste heat, which makes sufficient cooling necessary.

SUMMARY

The object of the invention is therefore to create an endoscope which in particular has a CMOS image sensor and LEDs and provides sufficient cooling.

This object is achieved by an endoscope having one or more features of the invention.

In this endoscope, a rotatably mounted heat sink is arranged in the handle, and a heat transmission element is arranged in the endoscope shaft, wherein the distal end of the heat transmission element is thermally coupled to the image sensor for conjoint rotation therewith, and the proximal end of the heat transmission element is thermally coupled to the heat sink and connected to the latter for conjoint rotation therewith.

The heat transmission element transports heat from the image sensor to the heat sink and thus prevents the distal region of the endoscope shaft from overheating, and the regulatory standards are thus satisfied. The heat transmission element is therefore preferably made of a material with very low thermal resistance and with the highest possible heat capacity, for example aluminum, copper or ceramic.

It is particularly advantageous if a heat-conducting element is arranged between the image sensor and the heat transmission element. This heat-conducting element facilitates the structural integration of the image sensor and of the heat transmission element.

The image sensor, the heat transmission element and the heat sink thus form a rotatable unit. Since the heat sink and the image sensor are each connected to the heat transmission element for conjoint rotation therewith, it is possible to achieve very good heat contact with a low heat transmission resistance to the heat generator. It is particularly expedient if the heat transmission element is designed to transmit a torque from the heat sink to the image sensor. This requires a certain torsional stiffness of the material.

In an advantageous embodiment of the invention, the heat transmission element is designed as a heat tube or heat pipe. In a heat tube, the heat is transported by evaporation and condensation of a liquid medium. Such heat tubes are known per se and afford the advantage of having a very low heat resistance and, in contrast to solid-body heat transmitters, accelerate the heat transfer through the condensation process. This results in very efficient transmission of the waste heat arising in the image sensor to the heat sink. Moreover, heat tubes are isothermal over practically their entire length, such that the heat tube itself radiates practically no heat. This means that the endoscope shaft does not heat up to any appreciable extent along its entire length. The waste heat is therefore transported to the heat sink, where it is guided to the outside.

A further advantage of the heat tube is that it requires only small dimensions, for example 1 mm to 10 mm, in order to achieve a sufficient conduction of heat. In this way, the heat tube can be easily integrated into the endoscope shaft.

It is particularly advantageous if the heat tube is rod-shaped. Such rod-shaped heat tubes are available as ready-made components and are therefore cost effective.

In an advantageous embodiment of the invention, the image sensor is a CMOS image sensor. The latter has a higher output than CCD image sensors. The higher heat output of these CMOS image sensors is guided safely and reliably to the heat sink as a result of the improved heat conduction through the heat transmission element, such that the existing regulatory standards concerning heating of the endoscope tip can be satisfied.

It is also particularly advantageous if the illumination device has at least one light-emitting diode. Light-emitting diodes permit very good illumination of the image and are energy efficient. Moreover, arranging the illumination device in the distal end of the endoscope shaft has the advantage that it is only electrical lines that have to be routed through the endoscope shaft, not the fiber optics of an external light source.

The illumination device is expediently connected to the endoscope shaft for conjoint rotation therewith. This allows the illumination device to pivot along with the viewing field. This has the advantage that the illumination of the image does not vary with rotation and thus always remains constant.

Particularly when using high-power light-emitting diodes, the heat development of the illumination device likewise contributes to the heating of the endoscope tip.

In a particularly advantageous embodiment of the invention, the illumination device is thermally coupled to the heat transmission element. This has the advantage that the heat emitted by the illumination device is also transported to the heat sink via the heat transmission element. In this way, the illumination device can be dimensioned to be more powerful, and the illumination is therefore substantially improved.

The thermal coupling of the illumination device to the heat transmission element can be effected, for example, by structural parts of the endoscope shaft, for example an attachment for the illumination device.

However, it is particularly advantageous if the thermal coupling is effected via a heat sink. This ensures efficient heat conduction to the heat transmission element and thus prevents the heat from radiating in other undesired directions, particularly to an optics unit or to the distal end of the endoscope shaft.

As has already been described, it is advantageous if the illumination device is connected rigidly to the endoscope shaft. In this case, it is expedient if a thermally coupled rotary bearing, in particular a slide bearing, is formed between the distal end of the heat transmission element and the illumination device. Alternatively, the rotary bearing can also be formed between heat-conducting elements which are each connected to the illumination device and to the image sensor. This permits free rotatability of the heat transmission element and a low thermal resistance. The slide bearing can preferably be configured with a thermally conductive paste or coating in order to improve the heat conduction between the slide partners.

The heat introduced into the heat sink is released via the grip. To improve this release of heat, it is expedient if a heat transfer region is defined between the handle and the heat sink and permits heat transmission. Since the heat sink is rotatable relative to the handle, it is particularly advantageous if an air gap is formed between a handle wall and the heat sink. This air gap ensures the rotatability of the heat sink and a transmission of heat from the heat sink to the handle.

This air gap is preferably as narrow as possible, such that the air gap offers the lowest possible heat resistance.

In an advantageous embodiment, the heat sink is mounted rotatably relative to the endoscope handle at least at one point by a rotary bearing. Together with the rotary bearing in the endoscope tip, the unit composed of image sensor, heat transmission element and heat sink is thus clearly defined and is mounted rotatably inside the endoscope.

It is particularly advantageous if the heat sink has two axially spaced apart rotary bearings inside the endoscope handle. In this way, the heat sink is additionally supported inside the handle, as a result of which the endoscope is protected from the damage that could arise from the weight of the heat sink during movements.

The heat sink is preferably mounted by slide bearings and/or roller bearings. These have low friction and permit sufficient rotatability of the heat sink. For heat dissipation, it is particularly advantageous if they are mounted on both sides of the heat transfer region.

In the case of roller bearings, it may be advantageous that these have a higher thermal resistance than slide bearings. In this way, the heat transfer preferably takes place in the heat transfer region and not through the bearing. This also has the advantage that the bearing can be made more flexible, particularly also at locations where no heat transmission is intended to take place.

A narrow air gap is preferably arranged in the area of the heat transfer region. In an advantageous embodiment, the heat transfer region is formed by a thickening of the heat sink between and/or beyond the rotary bearings. This means that the diameter of the heat sink is greater in the heat transfer region than in the bearing.

At the same time, or alternatively, the heat transfer region can also be formed by a constriction of the housing. The housing diameter is preferably reduced here between the bearings.

It is important that a distance between the heat sink and/or the heat transmission element and the housing of the handle in the heat transfer region is smaller than a distance between the housing and the heat sink in the region of a bearing.

In a particularly expedient embodiment, the air gap is filled with a heat-conducting liquid, paste or powder. In this way, the thermal resistance of the air gap is considerably reduced, as a result of which the heat transfer from the heatsink to the handle is substantially improved.

This liquid can be, for example, a substantially liquid heat-conducting paste or boron nitride. However, it is also possible to use another medium with low thermal resistance, which does not prevent a rotational movement of the heat sink.

The handle of the endoscope generally has a substantially cylindrical shape. Accordingly, it is advantageous if the heat sink also has a rotationally symmetrical shape such that it is rotatable inside the handle. It is therefore expedient if the heat transfer region is formed radially with respect to the heat sink or formed axially in the proximal end region of the handle. This has the effect that the heat is carried away from the patient.

The image sensor is generally connected to an actuating device via which the position of the image sensor can be changed.

In an advantageous embodiment of the invention, the endoscope has an actuating device for the image sensor, which actuating device is connected to the image sensor via a toque coupling having the heat transmission element, and with which a torque can be transmitted form the outside to the torque coupling. This means that the actuating device acts on the rotatable unit comprised of image sensor, heat transmission element and heat sink by way of this torque coupling. This operative connection can be arranged at any desired location of the unit. For example, the actuating device can act on the heat sink or, in a proximal region, on the heat transmission element.

The actuating device is expediently arranged outside the wall of the handle or of the endoscope shaft. This permits simple handling of the actuating device. In addition, the endoscope shaft and the handle can have a closed and substantially sealed configuration, since only a small opening is needed for the actuating device.

In one possible embodiment, the actuating device is designed as a lever which is rigidly connected to the heatsink and protrudes radially from the housing. In an alternative embodiment, the actuating device is designed as a rotary wheel, which is guided axially from the handle at the proximal end of the handle.

In a particularly advantageous embodiment, the actuating device is arrange outside the heat transfer region. This has the advantage that the heat transfer region is not interrupted by an actuating device and thus offers better heat transmission.

In a particularly advantageous embodiment of the invention, the actuating device is designed as a magnetic actuating device. The actuating device is in this case expediently arranged outside the handle and connected to the torque coupling via a magnetic connection. This has the advantage that the housing of the handle can be completely closed and encapsulated, since no opening is needed for the passage of a torque coupling.

The advantage of this is that there is no need for complicated sealing of the handle or of a housing opening. This is particularly advantageous if, in order to provide better heat transmission, the air gap between heat sink and handle wall is filled with a liquid medium.

In a further advantageous embodiment of the invention, a heat-conducting element is arranged between the image sensor and the heat transmission element, which heat-conducting element is spaced apart or separated from the endoscope shaft by an insulating layer. This prevents a situation where heat from the image sensor not reaching the heat transmission element is radiated off. This in particular prevents the endoscope tip from heating beyond what is permitted by the standard regulations.

In addition to the endoscope according to the invention, the invention also comprises the use of a heat transmission element in an endoscope, wherein the distal end of the heat transmission element is thermally coupled to an image sensor and connected to the latter for conjoint rotation therewith, and the proximal end of the heat transmission element is thermally coupled to a heat sink and connected to the latter for conjoint rotation therewith, and the image sensor and the heat sink are each mounted rotatably.

BRIEF DESCRIPTION OF THE DRAWINGS

The invention is explained in more detail below on the basis of an illustrative embodiment and with reference to the attached drawings, in which.

DETAILED DESCRIPTION

Figure 1:
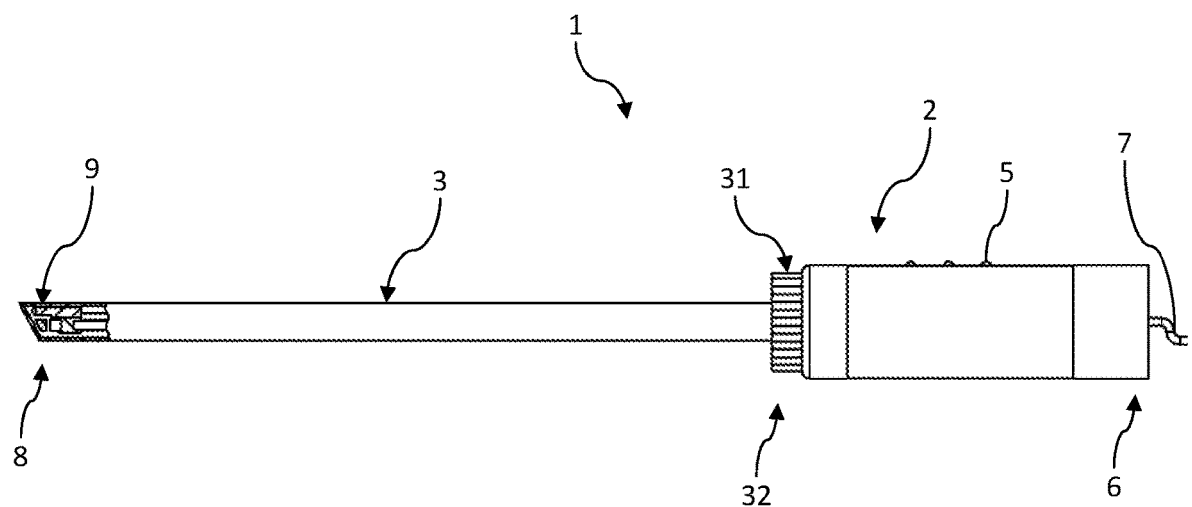
FIG. 1 shows a side view of an endoscope according to the invention.
Figure 2:
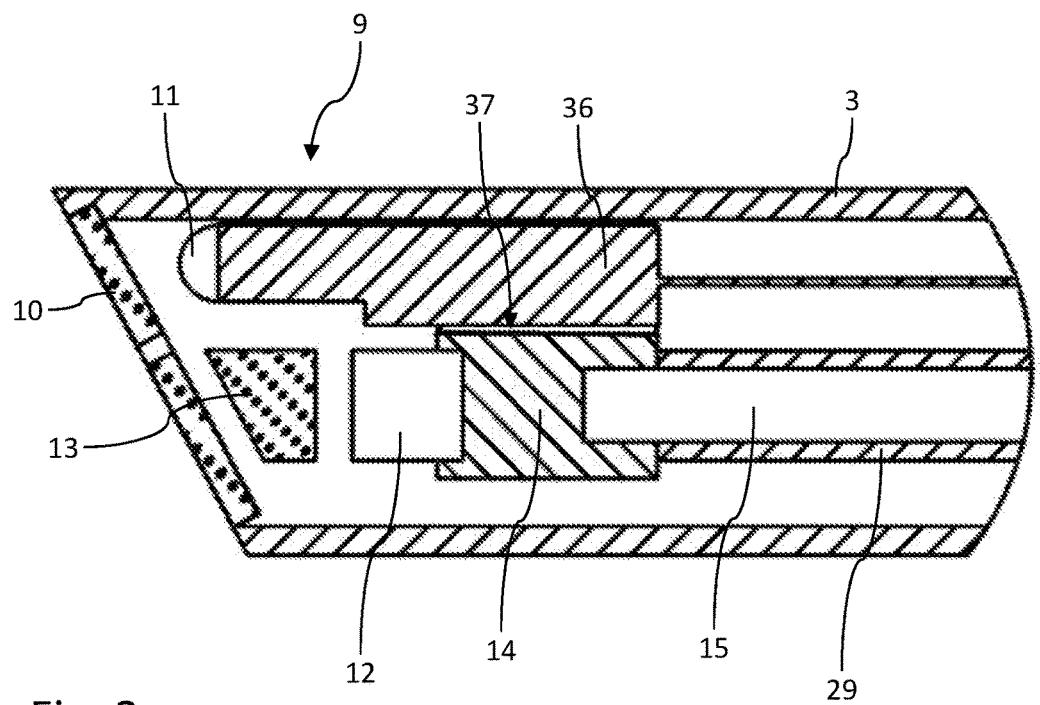
FIG. 2 shows a detailed view of the endoscope tip.

FIG. 1 shows an endoscope 1 according to the invention. The endoscope 1 principally has an endoscope handle 2 and an endoscope shaft 3.

The endoscope handle 2 has a handgrip 4 at which the endoscope can be held. In the example, control elements 5 are arranged at the handgrip 4, for example for the illumination or the camera. At the proximal end 6 of the endoscope handle 2, a cable 7 is arranged via which video signals and the current supply are fed.

The endoscope shaft 3 is connected to the endoscope handle 2 for conjoint rotation therewith. Located at the distal end 8 of the endoscope shaft 3 is the endoscope tip 9, which has an oblique viewing window 10. An illumination device 11 is arranged in the interior of the endoscope tip 9, and the light of the illumination device 11 can exit through the viewing window 10. For better heat dissipation, the illumination device 11 is secured on a heat-conducting element 36, which is rigidly connected to the endoscope shaft 3. An image sensor 12 is arranged next to the illumination device 11. Arranged between the viewing window 10 and the image sensor 12 is a prism unit 13, by which light entering through the viewing window 10 is conveyed onto the image sensor 12.

For better heat dissipation, the image sensor 12 is likewise mounted on a heat-conducting element 14. In the proximal direction, the heat-conducting element 14 is thermally coupled to a heat pipe 15 (heat tube) as heat transmission element and is mechanically connected to the latter for conjoint rotation therewith. A heat pipe 15 is known in principle in the prior art, for which reason its function is not explained in any further detail here. The heat pipe 15 used in the example is designed as a straight tube or straight rod and is commercially available, for example as a ready-made accessory. A heat-transmitting slide bearing 37 is arranged between the heat-conducting element 36 of the illumination device 11 and the heat-conducting element 14 of the image sensor 12. This slide bearing 37 permits, on the one hand, the rotatability of the image sensor 12 with respect to the endoscope shaft 3 and, on the other hand, an additional heat dissipation from the illumination device 11 into the heat pipe 15.

The heat pipe 15 connects the image sensor 12 thermally to a heat sink 16 arranged in the endoscope handle 2.

Figure 3:
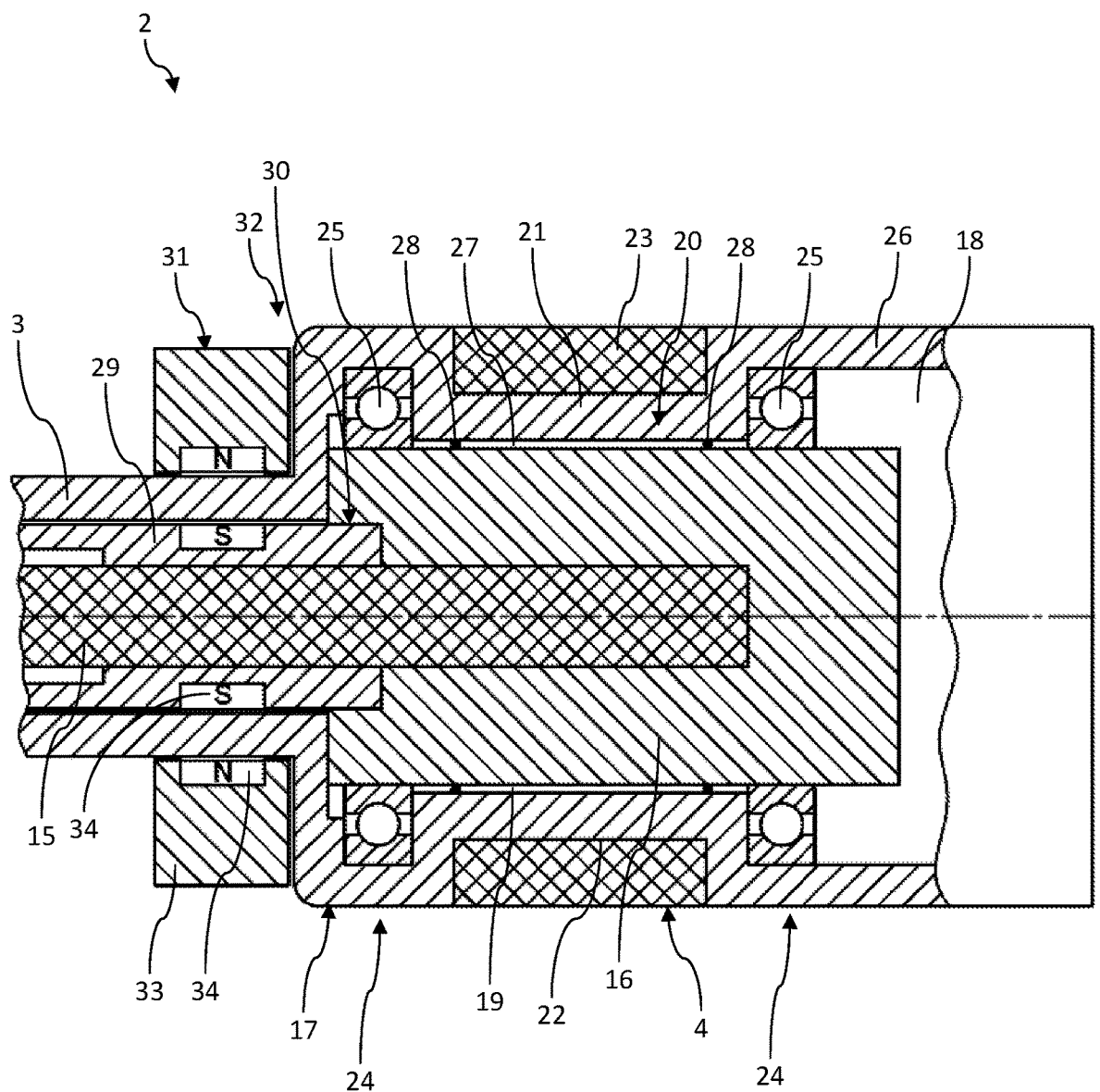
FIG. 3 shows a sectional view of an endoscope handle according to a first embodiment of the invention.

FIG. 3 now shows a first embodiment of an endoscope handle 2. The endoscope handle 2 has an approximately cylindrical housing 17, which forms an interior 18 in which a substantially cylindrical heat sink 16 is arranged.

An air gap 19 is formed between the housing 17 and the heat sink 16 and defines a heat transfer region 20 which allows heat to be transmitted from the heat sink 16 to the housing 17. In this embodiment, the heat transfer region 20 is formed by a constriction 21 of the housing 17. Arranged on the outer circumference 22 of the constriction 21 is a heat-insulating handle onlay 23 which forms the handgrip 4 and which prevents overheating of the handgrip 4.

At two bearing points 24 spaced axially apart from each other, the heat sink 16 is mounted rotatably with respect to the wall 26 of the housing 17 by ball bearings 25. In this example, the heat transfer region 20 is arranged between the two bearing points 24, and the bearing points 24 thus lie outside the heat transfer region 20. This in particular improves the heat transmission in the heat transfer region 20 and prevents unnecessary heating of the bearings 25.

To improve the heat transmission from the heat sink 16 to the housing 17, in this example the air gap 19 in the heat transfer region 20 is additionally filled with a heat-conducting liquid 27. This liquid 27 can be, for example, a substantially liquid heat-conducting paste or boron nitride. To ensure that the liquid 27 remains inside the air gap 19, the air gap 19 is sealed off on both sides by a respective seal 28. This seal 28 can also increase the resistance to the rotation of the heat sink 16, such that the heat sink 16 does not rotate automatically.

The heat pipe 15 is arranged coaxially in the center of the heat sink 16. The heat sink 16 thus serves as heat sink for the heat transported by the heat pipe 15. This heat is taken up by the heat sink 16 and transmitted to the surrounding housing 17 via the heat transfer region 20. The heat pipe 15 is rigidly connected to the heat sink 16 for conjoint rotation therewith.

The heat pipe 15 inside the endoscope shaft 3 is surrounded by a sleeve 29, which is likewise connected to the heat sink 16 and the heat pipe 15 for conjoint rotation with these and prevents excessive torque being placed on the heat pipe 15.

The heat sink 16, the heat pipe 15, the sleeve 29 and the image sensor 12 thus form a rigid unit as a torque coupling 30, which is rotatable as a whole.

For manual rotation of the torque coupling 30, the endoscope 1 has a magnetic actuating device 31, which is connected to the image sensor 12 via the torque coupling 30.

The actuating device 31 is arranged at the proximal end 32 of the endoscope shaft 3, directly in front of the endoscope handle 2. This device is configured in the example as an actuating ring 33, which coaxially encloses the cylindrical endoscope shaft 3. Arranged on the inner circumference of the actuating ring 33 is a multipolar ring magnet 34, which is alternately magnetized in the circumferential direction. This means that the north and south poles of the ring magnet 34 lie next to one another in alternation in the circumferential direction.

Arranged opposite this ring magnet 34, on the outer circumference of the sleeve 29, there is likewise a ring magnet 34 which, in terms of the number of poles and magnetization, is of identical configuration to the ring magnet 34 of the actuating device 30. The north and south poles of each of the two ring magnets 34 are oriented radially. In this way, the actuating ring 33 is connected magnetically to the sleeve 29. If the actuating ring 33 is now rotated manually, the magnetic coupling causes a rotation of the sleeve and therefore of the entire torque coupling 30. In this way, the image sensor 12, being part of the torque coupling, can be rotated with respect to the endoscope shaft 3 and the endoscope handle 2. This magnetic actuating device 30 has the advantage that it lies in particular outside the heat transfer region 20 and thus does not adversely affect the heat dissipation. In addition, the endoscope 1 can be of a completely closed design.

Figure 4:
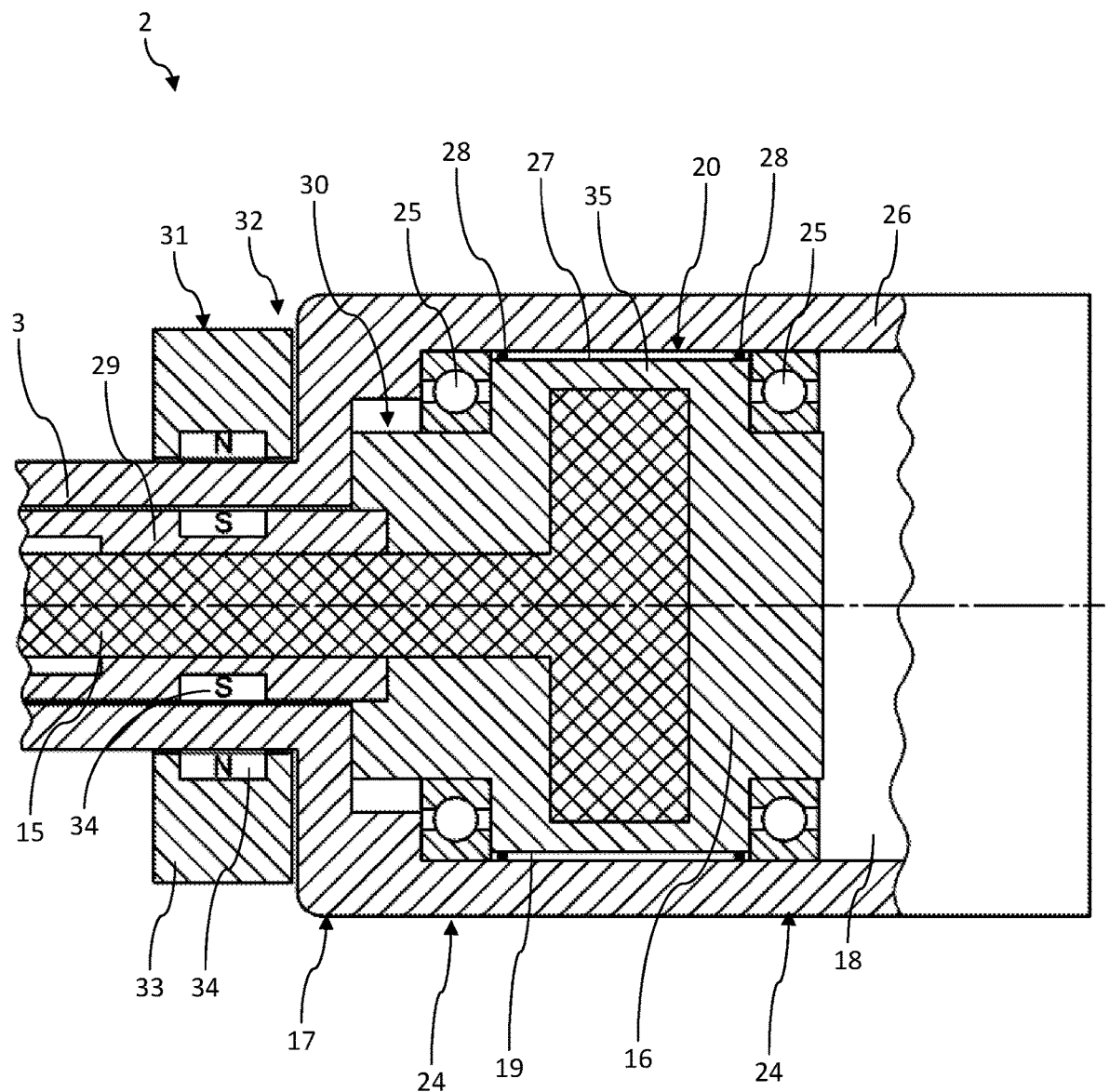
FIG. 4 shows a sectional view of an endoscope handle according to a second embodiment of the invention.

FIG. 4 shows an alternative embodiment of the endoscope handle 2, which corresponds substantially to FIG. 3. However, in this embodiment, the heat transfer region 20 is not formed by a constriction of the housing 17, but by a thickening 35 of the heat sink 16 between the bearing points 24.

Figure 5:
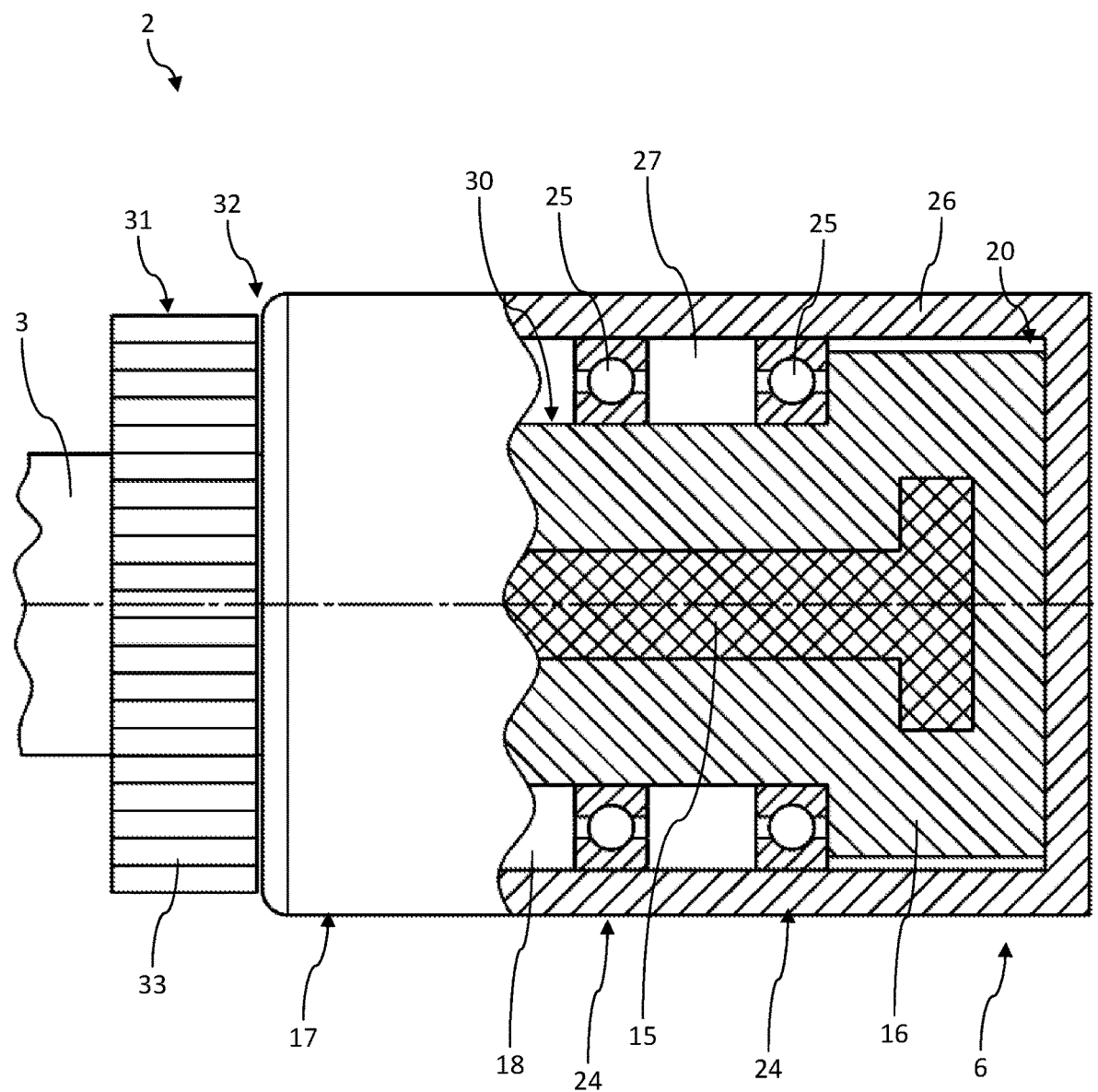
FIG. 5 shows a sectional view of an endoscope handle according to a third embodiment of the invention.

In the alternative shown in FIG. 5, the heat transfer region 20 is formed axially at the proximal end 6 of the endoscope handle 2. In this embodiment too, the heat sink 16 is mounted rotatably at two bearing points 24. However, these two bearing points 24 are in this case arranged distally in front of the heat transfer region 20.

The invention thus describes an endoscope 1 with an endoscope shaft 3 in which an illumination device 11 and a rotatably mounted image sensor 12 are arranged in a distal region, and with an endoscope handle 2 in which a rotatably mounted heat sink 16 is arranged, wherein the image sensor 12 is thermally connected to the heat sink 16, for conjoint rotation therewith, via a heat transmission element 15.

LIST OF REFERENCE SIGNS 1 endoscope
2 endoscope handle
3 endoscope shaft
4 handgrip
5 control elements
6 proximal end of the endoscope handle
7 cable
8 distal end of the endoscope shaft
9 endoscope tip
10 viewing window
11 illumination device
12 image sensor
13 prism unit
14 heat-conducting element of the image sensor
15 heat pipe
16 heat sink
17 housing
18 interior
19 air gap
20 heat transmission region
21 constriction
22 outer circumference of the constriction
23 handgrip onlay
24 bearing point
25 ball bearing
26 housing wall
27 liquid
28 seal
29 sleeve
30 torque coupling
31 actuating device
32 proximal end of the endoscope shaft
33 actuating ring
34 ring magnet
35 thickening
36 heat-conducting element of the illumination device
37 slide bearing

The invention claimed is:

1. An endoscope comprising:
an endoscope shaft having a proximal end and a distal region;
an illumination device and an image sensor located in the distal region and mounted rotatably with respect to the endoscope shaft;
an endoscope handle connected to the proximal end;
a heat sink arranged in the endoscope handle, the heat sink being rotatably mounted in the endoscope handle at least at one bearing point by at least one rotary bearing;
a heat transmission element is arranged in the endoscope shaft, with a distal end of the heat transmission element thermally coupled to the image sensor, and a proximal end of the heat transmission element thermally coupled to the heat sink and connected to the heat sink for conjoint rotation therewith.

2. The endoscope as claimed in claim 1, wherein the heat transmission element is at least one of a heat tube or rod-shaped.

3. The endoscope as claimed in claim 1, wherein the image sensor is connected to the heat transmission element for conjoint rotation therewith.

4. The endoscope as claimed in claim 1, wherein a heat-conducting element is arranged between the image sensor and the heat transmission element.

5. The endoscope as claimed in claim 1, wherein the image sensor is a CMOS image sensor.

6. The endoscope as claimed in claim 1, wherein the illumination device has at least one light-emitting diode.

7. The endoscope as claimed in claim 1, wherein the illumination device is thermally coupled to the heat transmission element.

8. The endoscope as claimed in claim 1, wherein a thermally coupled rotary bearing is formed between the distal end of the heat transmission element or of the heat-conducting element and the illumination device or the heat-conducting element.

9. The endoscope as claimed in claim 1, wherein a heat transfer region is defined between the endoscope handle and the heat sink and permits heat transmission by an air gap being formed between a housing wall and the heat sink.

10. The endoscope as claimed in claim 9, wherein the air gap is filled with a heat-conducting liquid.

11. The endoscope as claimed in claim 1, wherein the heat sink is mounted in the endoscope handle at least two bearing points by slide or roller bearings on both sides of the heat transfer region.

12. The endoscope as claimed in claim 11, wherein the heat transfer region is formed by a thickening of the heat sink at least one of between or beyond the slide or roller bearings or by a constriction of the housing, and a distance between at least one of the heat sink or the heat transmission element and the housing of the endoscope handle in the heat transfer region is smaller than a distance between the housing and the heat sink in a region of one of the bearing points.

13. The endoscope as claimed in claim 1, wherein the heat transfer region is formed radially with respect to the heat sink or formed axially in the proximal end region of the handle.

14. The endoscope as claimed in claim 1, wherein the endoscope includes an actuating device for the image sensor, said actuating device is connected to the image sensor via a torque coupling having the heat transmission element.

15. The endoscope as claimed in claim 1, further comprising an actuating device arranged outside a wall of the handle or on the endoscope shaft, said actuating device transmits a torque from outside to the torque coupling.

16. The endoscope as claimed in claim 1, further comprising a heat-conducting element arranged between the image sensor and the heat transmission element, said heat-conducting element is spaced apart or separated from the endoscope shaft by an insulating layer.

17. The endoscope as claimed in claim 1, wherein the illumination device is connected to the endoscope shaft for conjoint rotation therewith.

18. The endoscope as claimed in claim 1, wherein the illumination device is thermally coupled to the heat transmission element by a heat-conducting element.

19. A method of removing heat from an endoscope, comprising:
   thermally coupling a distal end of a heat transmission element to an image sensor and connecting the image sensor to for conjoint rotation therewith;
   thermally coupling a proximal end of the heat transmission element to a heat sink that is rotatably mounted in the endoscope handle at least at one bearing point by at least one rotary bearing and connecting the heat transmission element for conjoint rotation therewith; and
   rotatably mounting the image sensor and the heat sink in a shaft of the endoscope.

* * * * *